United States Patent
Conti et al.

(10) Patent No.: US 9,421,190 B2
(45) Date of Patent: Aug. 23, 2016

(54) COMPOSITIONS COMPRISING AMINO ACIDS FOR PREVENTION AND/OR TREATMENT OF RENAL DISORDERS

(71) Applicants: DETERMINANTS OF METABOLISM RESEARCH LABORATORY S.R.L., Castel San Giovanni (PC) (IT); Giovanni Federico Maria Conti, Milan (IT); Edoardo Carlo Maria Conti, Milan (IT); Isabella Arborio Mella, Milan (IT)

(72) Inventors: Franco Conti, Milan (IT); Francesco Saverio Dioguardi, Milan (IT)

(73) Assignee: DETERMINANTS OF METABOLISM RESEARCH LABORATORY S.R.L., Castel San Giovanni (PC) (IT)

( * ) Notice: Subject to any disclaimer, the term of this patent is extended or adjusted under 35 U.S.C. 154(b) by 0 days.

(21) Appl. No.: 14/225,556

(22) Filed: Mar. 26, 2014

(65) Prior Publication Data

US 2014/0206736 A1    Jul. 24, 2014

Related U.S. Application Data

(62) Division of application No. 13/521,937, filed as application No. PCT/IB2011/050132 on Jan. 12, 2011, now abandoned.

(30) Foreign Application Priority Data

Jan. 12, 2010   (IT) .............................. TO2010A0012

(51) Int. Cl.
| | |
|---|---|
| *A61K 31/198* | (2006.01) |
| *A61K 31/4172* | (2006.01) |
| *A61K 31/405* | (2006.01) |
| *A23L 1/305* | (2006.01) |
| *A61K 45/06* | (2006.01) |

(52) U.S. Cl.
CPC ............ *A61K 31/405* (2013.01); *A23L 1/3051* (2013.01); *A61K 31/198* (2013.01); *A61K 31/4172* (2013.01); *A61K 45/06* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 5,728,678 A * | 3/1998 | Trimbo et al. ................. | 514/5.5 |
| 6,218,420 B1 | 4/2001 | Dioguardi | |
| 2003/0187049 A1 | 10/2003 | Dioguardi | |
| 2004/0192756 A1 * | 9/2004 | Conti et al. .................... | 514/419 |
| 2005/0239888 A1 | 10/2005 | Franzone et al. | |

FOREIGN PATENT DOCUMENTS

| | | |
|---|---|---|
| EP | 0 747 395 | 12/1996 |
| GB | 1 444 621 | 8/1975 |
| WO | WO 98/26774 | 6/1998 |
| WO | WO 02/02092 | 1/2002 |
| WO | WO 0202092 A2 | 1/2002 |
| WO | WO 2004/012706 | 2/2004 |
| WO | WO 2005034932 A2 * | 4/2005 |

OTHER PUBLICATIONS

U.S. Appl. No. 12/996,426, filed Mar. 2011, Conti et al.
International Search Report for PCT/IB2011/050132 mailed Mar. 29, 2011.
Written Opinion of the International Searching Authority mailed Mar. 29, 2011.
Database WPI, Week 200874, Thomson Scientific, XP002596114, Oct. 16, 2008, Retrieved Aug. 13, 2010, 2 pages.
Database WPI, Week 200275, Thomson Scientific, XP002596115, Sep. 26, 2002, Retrieved Aug. 13, 2010, 4 pages.

\* cited by examiner

*Primary Examiner* — Svetlana M Ivanova (74) *Attorney, Agent, or Firm* — Nixon & Vanderhye P.C.

(57) ABSTRACT

Composition comprising leucine, isoleucine, valine, threonine and lysine for use in prophylactic and/or therapeutic treatment of renal disorders in a subject, preferably an elderly subject.

13 Claims, 4 Drawing Sheets

COMPOSITIONS COMPRISING AMINO ACIDS FOR PREVENTION AND/OR TREATMENT OF RENAL DISORDERS

CROSS REFERENCE

This application is a divisional of U.S. patent application Ser. No. 13/521,937, filed Jul. 12, 2012, pending, which is the U.S. national phase of International Application No. PCT/IB2011/050132, filed 12 Jan. 2011 which designated the U.S. and claims priority to IT TO2010A000012, filed 12 Jan. 2010, the entire contents of each of which are hereby incorporated by reference in this application.

FIELD OF THE INVENTION

The present invention regards compositions for prevention and/or treatment of renal disorders in mammals. More specifically, the present invention concerns the use of compositions for prevention and/or treatment of renal disorders comprising natural and non-natural amino acids preferably in an elderly subject.

BACKGROUND

Although human kidneys age better than other fundamental organs, such as the heart and brain, their decline in structure and function increases the susceptibility of healthy subjects as well as those with chronic disease to drugs and electrolyte abnormalities during stressful conditions. Chronic kidney diseases (CKD) and their progression to end-stage renal disease (ESRD) are considerable social and economic problems in all industrialized countries.

Each year in Italy, more than 18,000 patients are diagnosed as having CKD, and about a half million Italians have serum creatinine levels higher than 1.5 mg/dL. The incidence of CKD is strictly linked to age. A French epidemiological study indicated that the CKD incidence in patients over 75 years was almost 7 times that in patients aged 20-39 years and more the twice that in patients aged 40-59 years. Therefore, interventions that may prevent the development of CKD in middle age and the progression of CKD to ESRD are very important for public health.

Restricting protein in the diet of pregnant mice results in reduced numbers of nephrons in newborn animals greater than 30%. Low (LPD) or very low (VLPD) protein diets have been widely used, first for treating uremia and then to prevent the progression of CKD, but recently, a meta-analysis of existing data concluded that there is no evidence that LPD or VLPD diets have any effect in reducing the progression of kidney disease in diabetic nephropathy, and very often some degree of dangerous protein malnutrition occurs in these patients.

SUMMARY OF THE INVENTION

The present invention has the aim of providing new compositions for a prophylactic and therapeutic treatment, preferably but not exclusively intended for elderly subjects, of renal disorders.

According to the invention, the above object is achieved thanks to the subject matter recalled specifically in the ensuing claims, which are understood as forming an integral part of this disclosure.

In an embodiment, the composition described herein is particularly useful in the prophylactic and therapeutic treatment of renal disorders, and comprises a mixture of amino acids in free form suitable for use over a long period of time.

The inventor found, in fact, that the combination of some free amino acids is surprisingly efficient at preventing and/or treating renal diseases, like for example chronic kidney disease or renal failure in mammals. In a preferred application, such mixture improves renal filtration, particularly in elderly subjects.

Therefore, the present invention regards compositions based on amino acids for preventing and/or treating renal diseases in mammals having—as main active ingredients—the branched chain amino acid leucine in combination with at least one of, and preferably both, the branched chain amino acids isoleucine and valine. In a particular embodiment, the present invention concerns compositions comprising—as main active ingredients—the branched chain amino acids leucine, isoleucine and valine in combination with at least one of, and preferably both, threonine and lysine.

An advantage linked to the use of the compositions described herein lies in the high tolerability of the composition, which can be administered chronically. In a preferred embodiment, the administration may occur over a period of time sufficiently long to allow at least partial recovery of renal function.

A substantial advantage of the compositions subject of the invention is represented by the simple use of the same for the treated patients. The compositions are preferably produced, with or without excipients, according to known production, in formulations suitable for oral administration. In a preferred embodiment, the compositions described herein have a pH in aqueous solution comprised between 6.5 and 8.5, with or without excipients suitable for preparing tablets, capsules, powders, etcetera, through which a pharmacological performance suitable for oral administration is intended to be obtained. Also amino acids compositions produced, still according to per se known production techniques, for other types of administration shall be deemed comprised in the scope of the invention.

An advantage linked to the use of the composition described herein lies in the fact that the use of amino acids in free form allows producing such compositions at a comparatively extremely low cost with respect to proteins and growth factors synthesis, through per se known production processes and widely used in the field of preparing compositions based on free amino acids. The field of application of the invention may however also be extended to amino acids obtained through genetic engineering or any other artificial method.

BRIEF DESCRIPTION OF THE DRAWINGS

The invention will now be described, by way of example only, with reference to the enclosed figures of drawing, wherein.

DETAILED DESCRIPTION OF PREFERRED EMBODIMENTS

In the following description, numerous specific details are given to provide a thorough understanding of embodiments. The embodiments can be practiced without one or more of the specific details, or with other methods, components, materials, etc. In other instances, well-known structures, materials, or operations are not shown or described in detail to avoid obscuring aspects of the embodiments.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The headings provided herein are for convenience only and do not interpret the scope or meaning of the embodiments.

The compositions according to the invention (in the following referred as AA-compositions) comprise—as main active ingredients—the branched amino acid leucine in combination with at least one of, and preferably both, the branched amino acids isoleucine and valine. The preferred molar ratios of isoleucine and valine, with respect to one mole of leucine, are as follows:

isoleucine: from 0.2 to 0.7, preferably from 0.4 to 0.6;
valine: from 0.2 to 0.8, preferably from 0.4 to 0.7.

The inventor ascertained that the activity of the mixtures grew after adding at least one of, and preferably both, the amino acids threonine and lysine to the branched chain amino acids. More in detail, the preferred molar ratios of these amino acids, with respect to one mole of leucine, are as follows:

threonine: from 0.15 to 0.50, preferably from 0.2 to 0.45;
lysine: from 0.15 to 0.60, preferably from 0.3 to 0.55.

In particular, currently, the studies carried out by the inventor have demonstrated that the more efficient compositions are those in which, considering the sum of leucine, isoleucine and valine equal to 1, in the abovementioned stoichiometric ratio, then the sum of threonine and lysine is comprised between 0.10 and 0.50 (i.e. 1:0.10-0.50), still according to the molar weight, preferably between 0.25 and 0.45 (i.e. 1:0.25-0.45).

Studies carried out by the inventor have further shown that such compositions are more active in presence of further one or more essential amino acids selected from histidine, phenylalanine, methionine and tryptophan. Considering the sum of leucine, isoleucine, valine, threonine and lysine equan1 to 1, then the overall amount of the further essential amino acids may vary between 0.02 to 0.25 (i.e. 1:0.02-0.25), preferably from 0.05 to 0.15 (i.e. 1:0.05-0.15), still intended as the molar ratio.

The sum of the amount of threonine and lysine, still on the basis of the molecular weight, is preferably lower with respect to the sum of the single amounts of branched amino acids used, but greater with respect to the sum of the amount of the further essential amino acids used in the mixture. Furthermore, still preferably and on a molecular weight basis:

the amount of lysine is lower with respect to single amounts of the branched amino acids, but greater with respect to the single amounts of each of the further essential amino acids used in the mixtures (and hence even greater than the sum of the single amounts of such further essential amino acids, not considering threonine thereamong);

the amount of threonine is lower with respect to the single amounts of lysine and of the branched amino acids, but greater with respect to the single amounts of the further essential amino acids used in the mixtures, and much more preferably greater than the sum of the single amounts of the further essential amino acids.

In case methionine is used, the activity of the mixtures may be further enhanced by also providing for the insertion of the non-essential amino acid cystine (and/or cysteine) into the composition, in an amount of moles at least equivalent to that of methionine, and preferably comprised between 150 and 350% of methionine.

Alongside the abovementioned amino acids the AA-compositions described herein may also comprise the non-essential amino acid tyrosine, whose ideal amount shall be comprised between 15 and 50%, preferably between 20 and 35%, of the amount of phenylalanine in moles.

Though the AA-compositions may possibly comprise other amino acids with respect to the ones described above, the overall amount of said other amino acids shall not exceed 20% of the total of the active ingredients, and/or not exceed 10% per each single said other amino acid (still in molar weight). Furthermore, in particular, when preparing the AA-compositions according to the invention, the amino acids serine, proline, glycine, alanine, glutamic acid and, above all, arginine, are preferably avoided, given that they can be counterproductive or even harmful in some concentrations or stoichiometric ratios with the said formulation.

The amino acids used in the experimentation that led to the identification of the indicated ratios are those of the levogyrous type, corresponding to those present in nature and which are thus to be considered the preferred active form. However, the inventor ascertained that also the racemic form may perform the same activity, though in a lower manner proportional to the d-form percentage. Also the active derivatives of the indicated amino acids, in particular the salts thereof, shall obviously be deemed falling within the scope of the present invention.

Further specifications, in terms of amounts and ratios among the various amino acids provided for by the compositions for prevention and/or treatment of renal diseases are contained in the attached claims, which form an integral part of the technical teaching provided herein in relation to the invention.

Though expressed on the basis of molecular weight (i.e. in moles), the ratios indicated are applicable, in general terms, also in case of calculation according to the weight in grams of the various amino acids indicated (however bearing in mind that the amount of lysine, expressed in grams, may then be greater with respect to the single amounts of isoleucine and valine).

In the aged kidney, progressive glomerulosclerosis, and reduced glomerular filtration rate, all occur concomitantly with the loss of functioning nephrons, so that elderly kidneys are more susceptible to failure when other insults are superimposed.

The main findings of the instant description in the kidney after prolonged AA-composition intake in M-aged animals were 1) very scarce fibrosis limited to the interstitium and glomeruli; 2) increases in glomerular perfusion markers such as eNOS and VEGF and 3) recovery and/or maintenance of renal function also in elderly subjects.

To better understand the renal effects of dietary AA-composition intake in middle-aged rats the present inventor assessed changes in the glomerular, and tubular compartments with a combined morphological/morphometric, histochemical, and immunohistochemical approach.

The present inventor demonstrated in the instant description that in M-aged rats chronic AA-composition supplementation prevents the onset of morphological changes during the early stages of senescence. In particular, by using high-resolution morphometry on semi-thin sections reduced glomerular tufts was detected in the M-aged group that were restored after AA-composition supplementation to the form in younger rats.

In conclusion, the present data show that prolonged administration of a AA-composition have beneficial effects on kidney metabolism of M-aged rats, mainly retarding the typical alterations seen in senescence. AA-composition supplementation in the diet is a new strategy for maintaining a healthy renal status to prevent renal disorders and improve the quality of life.

Materials and Methods

Animals. The experimental protocol was approved and conducted in accordance with the Italian Ministry of Health and complied with the *The National Animal Protection Guidelines*. Seventeen male Wistar rats were used: 5 young (2-month-old) animals, and 12 middle-aged (M-aged; 18-month-old) animals.

The animals were caged separately. M-aged animals were divided into 2 groups: control group (M-aged, n=6) and AA-composition treated group (M-aged+AA, n=6). The animals were placed in a quiet room with the temperature and humidity controlled. A 12/12-h light/dark cycle was maintained (lights on from 7 a.m. to 7 p.m.). The rats were fed a standard diet ad libitum (18.8% protein content; Dottori Piccioni, Gessate, Milan, Italy) with water ad libitum (control M-aged and young groups) or a diet supplemented with AA-composition in the form of a solution (M-aged+AA group) that provided 1.5 g/kg per day of AA-compositions in the drinking water for 90 days. The concentration of the AA-composition in the drinking water was adjusted to the average daily water consumption of the rats (about 25 mL) and mimicked the recommended daily dose for humans (1). The composition of AA-composition used in the present experiments is shown in Table 1. The body weight and water or AA-composition consumption of each animal were monitored daily.

At the end of the treatments, the animals were killed under deep ether anesthesia. The kidneys were quickly removed and placed in an ice-cold saline solution. The samples used for histochemical analysis were carefully mounted in Tissue-tek® OCT (Sakura Finetek Europe, the Netherlands) embedding medium before they were frozen in liquid nitrogen and stored at −80° C.

AA-Composition. The composition of AA-composition used in the present experiments is shown in Table 1.

TABLE 1

| Amino acid | Molecular weight* | g/100 g | % on Tot. | % on group |
|---|---|---|---|---|
| L-Leucine | 131.17 | 31.2500 | 31.25% | 50.00% |
| L-Isoleucine | 131.17 | 15.6250 | 15.63% | 25.00% |
| L-Valine | 117.15 | 15.6250 | 15.63% | 25.00% |
| Branched group | | 62.5000 | 62.50% | 100.00% |
| L-Lysine | 146.19 | 16.2500 | 16.25% | 65.00% |
| L-Threonine | 119.12 | 8.7500 | 8.75% | 35.00% |
| Lysine + threonine group | | 25.0000 | 25.00% | 100.00% |
| L-Histidine | 155.16 | 3.7500 | 3.75% | 46.88% |
| L-Phenylalanine | 165.19 | 2.5000 | 2.50% | 31.25% |
| L-Methionine | 149.21 | 1.2500 | 1.25% | 15.63% |
| L-Tryptophan | 204.23 | 0.5000 | 0.50% | 6.25% |
| Further essentials group | | 8.0000 | 8.00% | 100.00% |
| L-Tyrosine | 181.19 | 0.7500 | 0.75% | |
| L-Cystine | 240.30 | 3.7500 | 3.75% | |
| Total composition | | 100.0000 | 100.00% | |

*from "Amino Acid, Nucleic Acids & Related Compounds - Specification/General Tests", 8th Edition, Kyowa Hakkco Kogyo Co., Ltd.

In the following table, the amounts of AA-composition in grams according to Table 1 are expressed according to the molecular weight, i.e. in moles.

TABLE 2

| Amino acid | Molecular weight | Mol | % on Tot. | % on group |
|---|---|---|---|---|
| L-Leucine | 131.17 | 0.23824 | 31.97% | 48.55% |
| L-Isoleucine | 131.17 | 0.11912 | 15.98% | 24.27% |
| L-Valine | 117.15 | 0.13338 | 17.90% | 27.18% |
| Branched group | | 0.49074 | 65.85% | 100.00% |
| L-Lysine | 146.19 | 0.11116 | 14.92% | 60.21% |
| L-Threonine | 119.12 | 0.07346 | 9.86% | 39.79% |
| Lysine + threonine group | | 0.18461 | 24.77% | 100.00% |
| L-Histidine | 155.16 | 0.02417 | 3.24% | 48.21% |
| L-Phenylalanine | 165.19 | 0.01513 | 2.03% | 30.19% |
| L-Methionine | 149.21 | 0.00838 | 1.12% | 16.71% |
| L-Tryptophan | 204.23 | 0.00245 | 0.33% | 4.88% |
| Further essentials group | | 0.05013 | 6.73% | 100.00% |
| L-Tyrosine | 181.19 | 0.00414 | 0.56% | |
| L-Cystine | 240.30 | 0.01561 | 2.09% | |
| Total composition | | 0.74522 | 100.00% | |

As observable from Table 1, the weight ratios between leucine, isoleucine and valine are preferably equivalent to 2:1:1. Table 1 and Table 2 also show that the single amounts (weight in grams or moles) of histidine, phenylalanine, methionine and tryptophan are preferably decreasing (i.e. the amount of histidine is greater than phenylalanine, which is greater than methionine, which is greater than tryptophan) and the amount (weight in grams or moles) of cystine (and/or cysteine) is preferably greater than tyrosine.

Renal Function-BUN Test. The present inventor performed a study—during a period of 20 months—directed to assess the renal function as blood urea nitrogen (BUN) by the Reflotron test (Roche Diagnostics, Indianapolis). Blood samples of control rats (control group) and rats supplemented with AA-composition (AA-treated group) for BUN determination were collected at different time intervals after cisplatin injection. BUN levels exceeding 30 mg/dl were considered abnormal.

Rats were from Charles River, Italy and the treatment was performed in accordance with the international guidelines. Male rats of 4 months were caged separately and divided in 2 groups (control and AA-composition treated group) of 40 animals each.

The rats were fed a standard diet ad libitum (18.8% protein content; Dottori Piccioni, Gessate, Milan, Italy) with water ad libitum (control group) or a diet supplemented with AA-composition in the form of a solution (AA-treated group) that provided 1 g/kg/day of AA-composition in the drinking water for 20 months. The composition of AA-composition used in the present experiment is shown in Table 1. The body weight and water or AA-composition consumption of each animal were monitored daily.

Transmission Electron Microscopy. One kidney from each animal were removed, fixed with 3% glutaraldehyde in PBS (pH 7.4, 0.1M), and postfixed for 1 hour with 1% $OsO_4$ in the same buffer. The samples were processed with standard procedures for embedding in Araldite (Sigma Chemical Co, Milan, Italy). Thick sections (about 1 µm) were stained with toluidine blue. Ultrathin sections (70 nm) were stained with a saturated aqueous solution of uranyl acetate and lead citrate and examined with a Philips CM10 electron microscope.

Morphometry. All measurements were obtained using standard morphometric techniques, as previously described (2, 3). The number of glomeruli (Nglo), the mean area of glomeruli (Aglo), the mean area of the renal corpuscle (Acor), and total area of the renal parenchyma (Atot) were evaluated on thick plastic sections stained with toluidine blue. From glomerular data the ratio between Aglo and Atot (Aglo/Atot) and the number of glomeruli per unit area, also called the glomerular density (Nglo/$mm^2$) were calculated.

Histochemistry

Sirius Red. Collagen deposition and fibrosis were evaluated by a Sirius Red staining method using a modified picrosirius procedure as previously described (4). Briefly, the sections were deparaffinized, rehydrated in distilled water, and immersed in 1% phosphomolybdic acid (Sigma-Aldrich, St. Louis, Mo., USA) for 5 min and then covered with 0.1% (w/v) Sirius Red F3B (C.I.35780 Science Lab, Huston, Tex., USA) in saturated picric acid solution for 1 h at room temperature. The sections were then washed in water and rapidly dehydrated, cleared in xylene, and mounted. All sections stained with Sirius Red were analyzed using a light microscope (Olympus BX50, Tokyo, Japan) under normal light and polarized light obtained with a polarizer filter (Olympus U-ANT, Tokyo, Japan) in order to analyze the initial collagen organization and the fibrosis, respectively. Under these conditions, collagen fibres of different thickness are coloured differently. Whereas the birefringent (anisotropic) colour is more a measure of collagen fibre size than of collagen type, usually the thicker and denser type I collagen fibres are detected as orange to red, whereas the thinner type III collagen fibres appear yellow to green (5, 6).

Immunohistochemistry. Sections were incubated overnight with primary anti-iNOS (NOS2-N20-sc651), anti-eNOS (NOS3-C20-sc654), or anti-VEGF (C-1-sc7269) polyclonal antibodies from Santa Cruz Biotechnology Inc. (Santa Cruz, Calif., USA) diluted 1:100 with PBS. The sections were processed in accordance with the manufacturers' protocols, visualized with a rabbit ABC-peroxidase staining system kit (Santa Cruz Biotechnology), and mounted with DPX. The reaction product was visualized using 0.3% $H_2O_2$ and DAB at room temperature. The immunohistochemistry control was performed by omitting the primary antibody in the presence of isotype-matched IgGs. To exclude incorrect interpretation of the immunostaining due to the presence of endogenous biotin (7), the present inventor also carried out experiments using the peroxidase-anti-peroxidase detection system, but obtained similar results. Each set of experiments was done in triplicate, with each replicate always carried out under the same experimental conditions.

The staining intensity on both histochemical and immunohistochemical slides was evaluated using an optical Olympus BX50 microscope equipped with an image analysis program (Image Pro Plus, Immagini e Computer, Milano, Italy) and analyzed quantitatively. The integrated optical density (IOD) was calculated for arbitrary areas, by measuring 10 fields for each sample using a 40× objective. Data were pooled to obtain a mean value, and a statistical analysis was applied to compare the results obtained from different experimental groups.

Statistics. Morphometric data are expressed as mean±SD unless otherwise stated. The statistical significance of the differences between means was assessed with one-way ANOVA followed by the Student-Newman-Keuls test or with a Student t-test. A probability of less than 5% (P<0.05) was considered significant.

Results

To test the effect of AA-composition on renal health, the diet of M-aged rats was supplemented with AA-composition dissolved in drinking water. Young and M-aged rats fed a standard diet were used as controls. At the end of the treatments, the young animals were 5 months old and the M-aged animals were 21 months. Body weight, kidney weight, and mean daily consumption of water and AA-composition in form of solution are summarized in Table 3. No significant differences in body or kidney weight between M-aged and M-aged+AA animals were observed (Table 3). The water and AA-composition intake did not differ between groups.

TABLE 3

|  | Body weights (g) | Kidney weights (g) | liquid consumption[a] (ml/day) |
|---|---|---|---|
| Young (n = 5) | 416 ± 12[b] | 3.4 ± 0.2 | 21.48 ± 3.6 |
| M-aged (n = 6) | 553 ± 27* | 4.1 ± 0.1* | 25.31 ± 4.1 |
| M-aged + AA (n = 6) | 577 ± 15* | 4.2 ± 0.3* | 23.02 ± 6.8 |
| F value | F = 104.86 | F = 8.66 | F = 2.57 |

[a]Young and M-aged rats consumed water, M-aged + AA consumed AA-composition dissolved in water.
[b]Values are given as mean ± SD.
*P < 0.05 versus young animals, Student-Newman-Keuls test.

Morphometry

Figure 1:
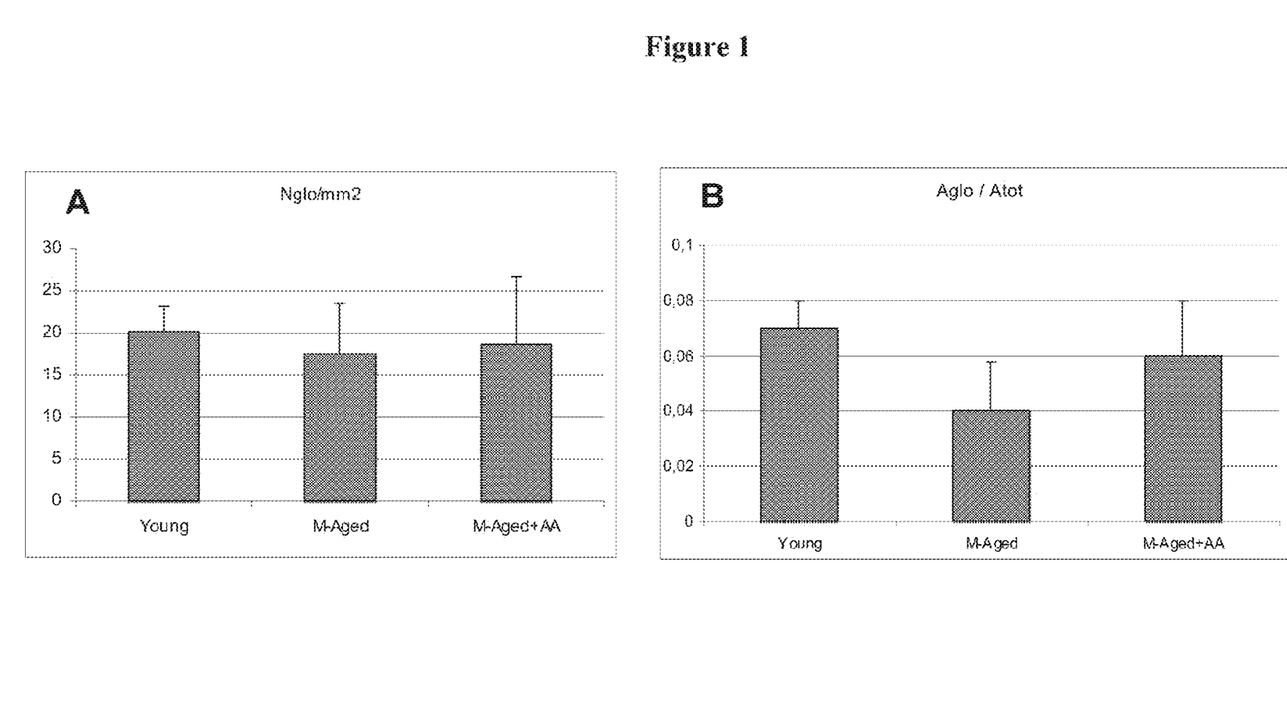
FIG. 1. A) Density of glomeruli (Nglo/mm$^2$) and B) ratio between glomerular area and total area (Aglo/Atot) in the 3 experimental groups. *$P<0.05$ versus young; ° $P<0.05$ versus M-aged, Student-Newman-Keuls test.

Glomeruli. The present inventor did not observe any significant differences of glomerular number (Nglo/$mm^2$) among groups. However, M-aged rats had significantly smaller glomeruli (Aglo), reflected in a reduction in Aglo/Atot of about 40% relative to young rats. Animals in the M-aged+AA group were not statistically different from young animals on these measures (FIG. 1).

Histology and Histochemistry

Sirius Red staining. The M-aged animals occasionally showed signs of interstitial fibrosis and glomerulosclerosis of moderate intensity. In contrast, the M-aged animals supplemented with AA-composition of table 1 did not show these morphological signs of incipient senescence.

Immunohistochemistry

Immunohistochemical staining for various markers in the three experimental groups were performed. The values are summarized in table 4, wherein integrated optical density values (±SD) in the three experimental groups are reported.

TABLE 4

|  | Young n = 5 | M-aged n = 6 | M-aged + AA n = 6 | F value |
|---|---|---|---|---|
| VEGF | 14 ± 2 | 4 ± 0.6* | 11 ± 1.4°* | 124.2 |
| eNOS | 53 ± 4.1 | 20 ± 2.3* | 45 ± 3.7°* | 55.99 |
| iNOS | 5 ± 1.1 | 13 ± 1.8* | 6 ± 0.8° | 38.52 |

*P < 0.05 versus young;
°P < 0.05 versus M-aged, Student-Newman-Keuls.

Vascular Marker (VEGF)

Figure 2:
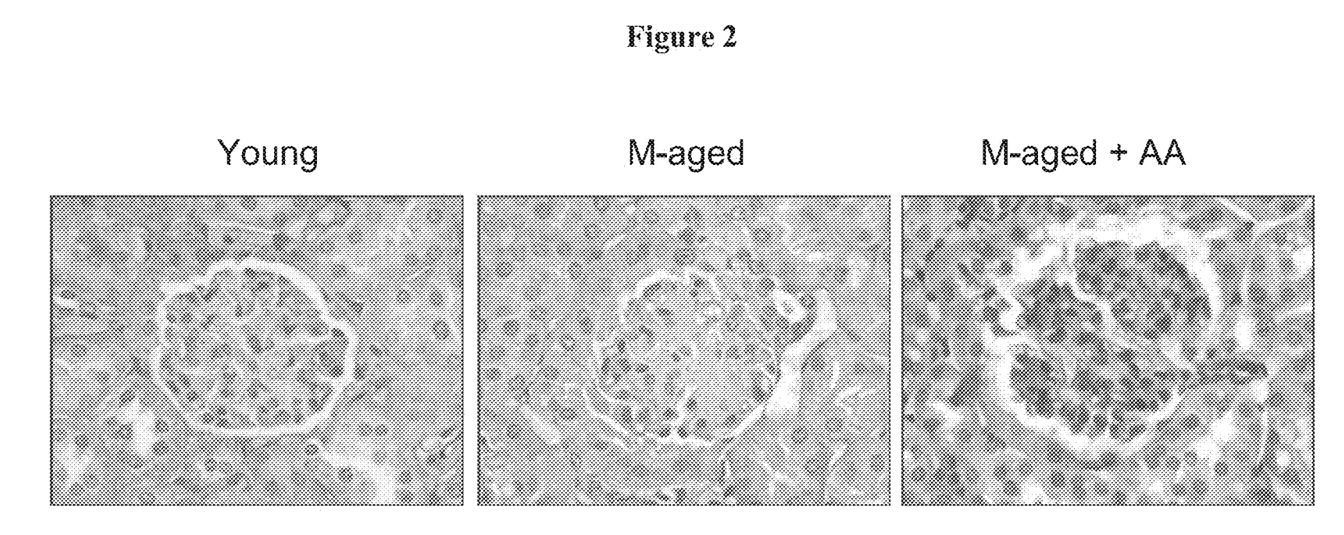
FIG. 2. VEGF immunohistochemistry (counterstained with hematoxylin). The M-aged animals expressed much less VEGF than young animals. After EAA supplementation, the VEGF immunostaining increased inside the glomerulus and inside the cells of Bowman's capsule. Scale bar, 100 µm.

M-aged animals showed significantly lower VEGF expression relative to young animals. In particular, the glomerular endothelia and Bowman's capsule cells of M-aged animals did not show VEGF expression. In contrast, the animals supplemented with AA-composition of table 1 showed intense VEGF expression mainly in glomeruli and to a lesser extent inside the Bowman's capsule cells (FIG. 2).

Nitrosactive Markers

Figure 3:
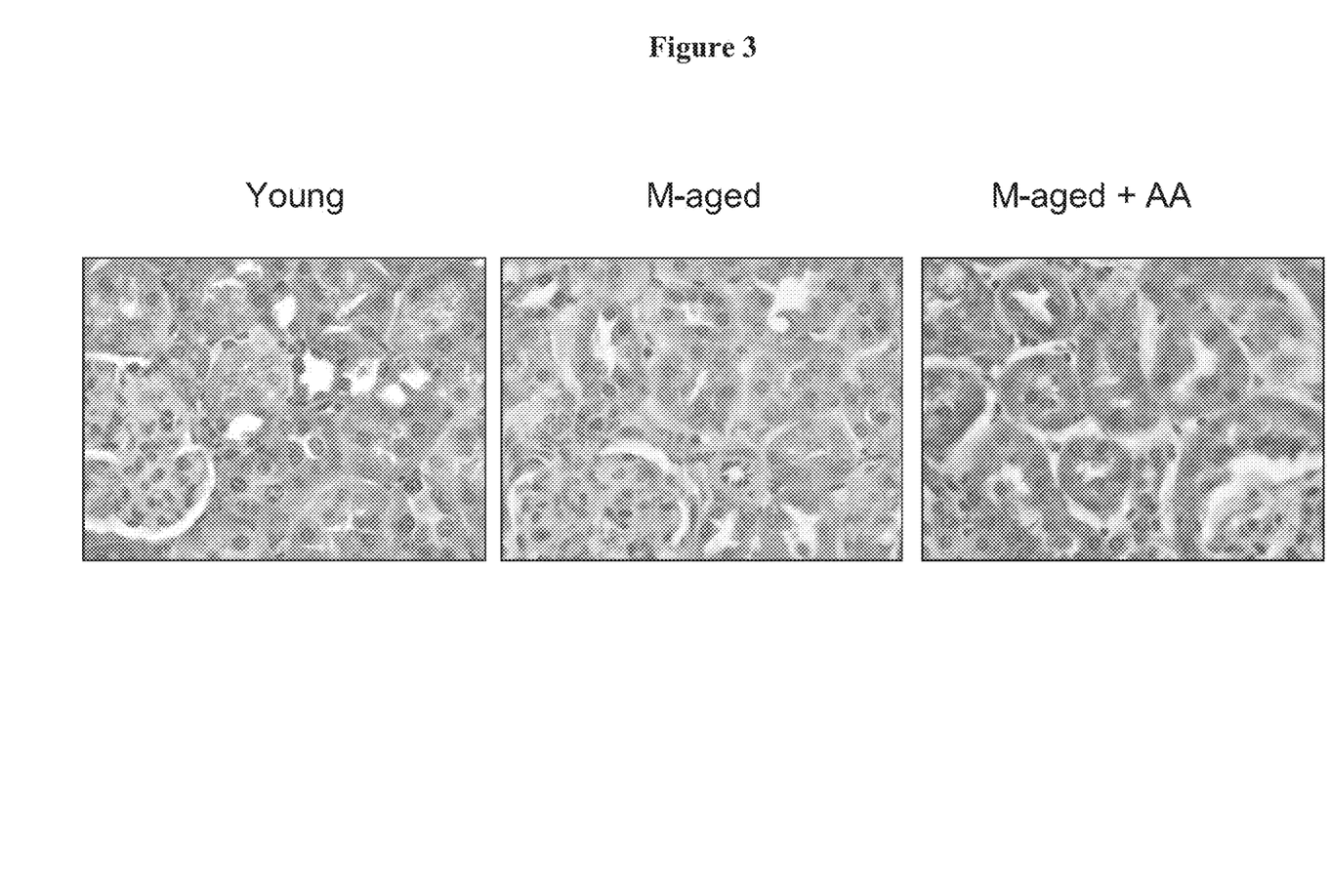
FIG. 3. eNOS immunohistochemistry (counterstained with hematoxylin). Young animals strongly expressed eNOS inside the tubular cells, whereas the expression decreased strongly in the M-aged animals. EAA supplementation restored the immunostaining in the tubular compartment to a level similar to that in the young group. Immunostaining was absent or very faint inside the glomeruli. Scale bar, 100 µm.

Endothelial nitric oxide synthase (eNOS). Inside the tubular cells of young animals, eNOS expression was very strong. In the M-aged animals, eNOS expression decreased, whereas AA-composition supplementation restored the intense immunostaining in the tubular compartment to levels similar to those in the young group. No or very faint immunostaining was seen inside the glomeruli in all experimental groups (FIG. 3).

Figure 4:
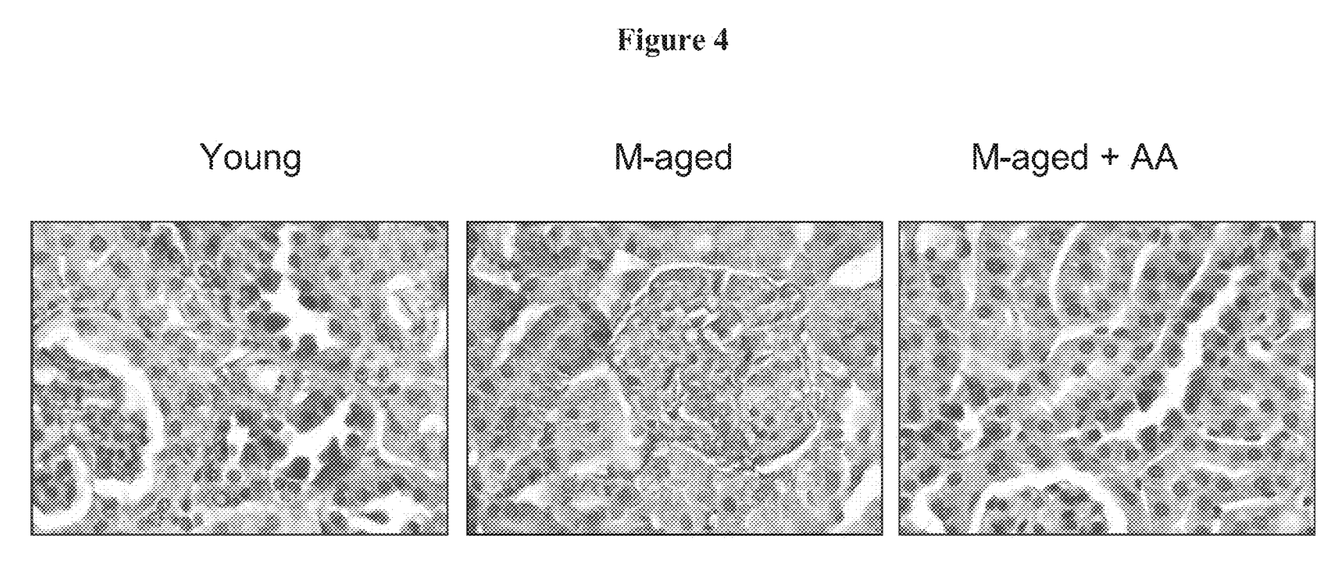
FIG. 4. iNOS immunohistochemistry (counterstained with hematoxylin). Young and EAA-fed M-aged animals showed intense iNOS expression only in some cells of distal tubules (star). The M-aged animals fed a standard diet showed intense immunostaining inside glomeruli and in the tubular compartment. Scale bar, 100 µm.

Inducible Nitric Oxide Synthase (iNOS). Young animals showed intense iNOS expression only in some cells of the distal tubules, whereas animals in the M-aged group showed increased expression in glomeruli and in the distal and proximal tubules. M-aged animals supplemented with AA-composition showed intense iNOS expression restricted to cells of the distal tubules and, as in young rats, no expression was seen inside the glomeruli or in other tubular cells (FIG. 4).

BUN Test

The present inventor observed a decrease of renal function of the control group during the 20 month period of treatment ($t_0$ to $t_4$), i.e. an increase of BUN, while the AA-treated group surprisingly maintained renal function within the limits (BUN<30 mg/dl). The data (expressed an mean±SD) are reported in table 5. At the end of the treatments, the animals were 24 months-old.

TABLE 5

|  | Parameters | Months of treatment | | | | |
|---|---|---|---|---|---|---|
|  |  | $t_0 = 0$ | $t_1 = 6$ | $t_2 = 10$ | $t_3 = 14$ | $t_4 = 20$ |
| Control | Body weight (g) | 24 ± 0.6 | 32 ± 2.1 | 37 ± 2.7 | 44 ± 3.1 | 46 ± 3.2 |
|  | BUN (mg/dl) | 23 ± 0.5 | 28 ± 0.8 | 32 ± 1.1 | 35 ± 1.3 | 39 ± 1.2 |
| AA- | Body weight (g) | 24 ± 0.7 | 31 ± 2.2 | 37 ± 2.5 | 43 ± 3.3 | 46 ± 3.4 |
|  | BUN (mg/dl) | 24 ± 0.4 | 25 ± 0.5 | 27 ± 0.7* | 29 ± 0.9** | 31 ± 1.1** |

*p < 0.05
**p < 0.01±

REFERENCES

1. Pellegrino M A, et al., Effects of voluntary wheel running and amino acid supplementation on skeletal muscle of mice. *Eur J Physiol* 2005; 93: 655-64.
2. Weibel E and Elias H. Quantitative methods in morphology. Berlin-Heidelberg, New York,: Springer-Verlag, 1987.
3. Corsetti G, et al., Ultrastructural study of the alterations in spinal ganglion cells of rats chronically fed on ethanol. *Ultrastructural Pathology* 1998; 22: 309-19.
4. Dayan D, et al., Are the polarization colors of picrosirius red-stained collagen determined only by the diameter of the fibers? *Histochemistry* 1989; 93: 27-9.
5. Vranes D, et al., Cellular mechanisms of diabetic vascular hypertrophy. *Microvasc Res* 1999; 57: 8-18.
6. Koren R, et al. Capsular collagen staining of follicular thyroid neoplasm by picrosirius red: role in differential diagnosis. *Acta Histochem* 2001; 103:151-157.
7. Nayler S, et al., Biotin inclusions: a potential pitfall in immunohistochemistry. *Histopathology* 1998; 33: 87-94.

The invention claimed is:

1. A method for treatment of a renal disorder comprising administering to a subject a composition comprising leucine, isoleucine, valine, threonine lysine, histidine, phenylalanine, methionine, tryptophan, tyrosine, and cysteine;
   wherein the leucine:isoleucine:valine weight ratio is substantially equivalent to 2:1:1;
   wherein the molar ratio of
   (threonine +lysine) : (leucine +isoleucine +valine)
   is between 1:0.10-0.50;
   wherein the molar ratio of
   (histidine +phenylalanine +methionine +tryptophan):(leucine +isoleucine +valine +threonine +lysine)
   is between 1:0.05-0.15; and
   wherein said composition is free of arginine, serine, proline, glycine, alanine, and glutamic acid.

2. The method according to claim 1, wherein the renal disorder is selected from the group consisting of: chronic kidney disease, end-stage renal disease, renal failure, diabetic nephropathy, glomerulonephritis, hydronephrosis, interstitial nephritis, and nephritic syndrome.

3. The method according to claim 1, wherein the composition is suitable for oral administration.

4. The method according to claim 1,
   wherein the leucine:isoleucine molar ratio is in the range of 1:0.2-0.7, and/or
   wherein the leucine:valine molar ratio is in the range of 1:0.2-0.8.

5. The method according to claim 1,
   wherein the leucine:isoleucine molar ratio is in the range of 1:0.4-0.6, and/or
   wherein the leucine:valine molar ratio is in the range of 1:0.4-0.7.

6. The method according to claim 1,
   wherein the leucine:threonine molar ratio is in the range of 1:0.15-0.50, and/or
   wherein the leucine:lysine molar ratio is in the range of 1:0.15-0.60.

7. The method according to claim 1,
   wherein the leucine:threonine molar ratio is in the range of 1:0.20-0.45, and/or wherein the leucine:lysine molar ratio is in the range of 1:0.30-0.55.

8. The method according to claim 1, wherein the ratio of (threonine +lysine):(leucine +isoleucine +valine) is 1:0.25-0.45.

9. The method according to claim 1,
wherein said composition comprises histidine, phenylalanine, methionine, and tryptophan,
wherein the ratio of
histidine, phenylalanine, methionine, and tryptophan) : (leucine, isoleucine, valine, threonine, and lysine) is 1:0.02-0.25.

10. The method according to claim 1, wherein said composition comprises methionine and cystine and/or cysteine, the methionine:cystine and/or cysteine molar ratio is in the range of 1:1-3.5.

11. The method according to claim 1, wherein said composition comprises phenylalanine and tyrosine, and the phenylalanine tyrosine molar ratio is 1:0.15-0.5.

12. The method according to claim 1, wherein said composition comprises phenylalanine and tyrosine, and the phenylalanine tyrosine molar ratio is 1:0.2-0.35.

13. The method according to claim 1, wherein said composition consists essentially of leucine, isoleucine, valine, threonine, lysine, histidine, phenylalanine, methionine, tryptophan, tyrosine and at least one of cysteine and cystine.

* * * * *